(12) United States Patent
Glandorf et al.

(10) Patent No.: US 12,427,097 B2
(45) Date of Patent: **\*Sep. 30, 2025**

(54) ORAL CARE COMPOSITIONS COMPRISING MONODENTATE AND POLYDENTATE LIGAND

(71) Applicant: The Procter & Gamble Company, Cincinnati, OH (US)

(72) Inventors: William Michael Glandorf, Mason, OH (US); Andrew Frederic Groth, Mason, OH (US); Samuel James St. John, Cincinnati, OH (US); Ross Strand, Singapore (SG)

(73) Assignee: The Procter & Gamble Company, Cincinnati, OH (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/886,244

(22) Filed: Sep. 16, 2024

(65) Prior Publication Data
US 2025/0009616 A1   Jan. 9, 2025

Related U.S. Application Data

(63) Continuation of application No. 17/308,081, filed on May 5, 2021, now abandoned.
(Continued)

(51) Int. Cl.
*A61K 8/27* (2006.01)
*A61K 8/06* (2006.01)
(Continued)

(52) U.S. Cl.
CPC .............. *A61K 8/27* (2013.01); *A61K 8/06* (2013.01); *A61K 8/21* (2013.01); *A61K 8/25* (2013.01);
(Continued)

(58) Field of Classification Search
CPC ... A61K 8/27; A61K 8/06; A61K 8/21; A61K 8/25; A61K 8/29; A61K 8/362;
(Continued)

(56) References Cited

U.S. PATENT DOCUMENTS 3,105,798 A \* 10/1963 Holliday .................. A61K 8/19
424/52
4,902,497 A    2/1990 Crisanti
(Continued)

FOREIGN PATENT DOCUMENTS

CN    104069013 A    10/2014
EP       2057978 A1     5/2009
(Continued)

OTHER PUBLICATIONS

First Office Action; Chinese Patent Application No. 202180033288.0 dated Jul. 27, 2023; 12 pages.
(Continued)

*Primary Examiner* — Marianne C Seidel
*Assistant Examiner* — Amanda Michelle Petritsch
(74) *Attorney, Agent, or Firm* — John G. Powell; Elizabeth Conklin

(57) ABSTRACT

Oral care compositions including tin, monodentate ligand, and polydentate ligand with an optimized molar ratio of tin to monodentate ligand to polydentate ligand. Oral care compositions with a tin to monodentate ligand to polydentate molar ratio of from about 1:0.5:0.5 to about 1:5:5. Oral care compositions including tin, monocarboxylic acid, and tricarboxylic acid.

17 Claims, 1 Drawing Sheet

Related U.S. Application Data

(60) Provisional application No. 63/020,032, filed on May 5, 2020.

(51) Int. Cl.

| | | |
|---|---|---|
| *A61K 8/21* | (2006.01) | |
| *A61K 8/25* | (2006.01) | |
| *A61K 8/29* | (2006.01) | |
| *A61K 8/362* | (2006.01) | |
| *A61K 8/365* | (2006.01) | |
| *A61K 8/37* | (2006.01) | |
| *A61K 8/55* | (2006.01) | |
| *A61K 8/60* | (2006.01) | |
| *A61K 8/73* | (2006.01) | |
| *A61Q 11/00* | (2006.01) | |

(52) U.S. Cl.
CPC ............. *A61K 8/29* (2013.01); *A61K 8/362* (2013.01); *A61K 8/365* (2013.01); *A61K 8/37* (2013.01); *A61K 8/55* (2013.01); *A61K 8/60* (2013.01); *A61K 8/73* (2013.01); *A61Q 11/00* (2013.01); *A61K 2800/48* (2013.01); *A61K 2800/74* (2013.01)

(58) Field of Classification Search
CPC . A61K 8/365; A61K 8/37; A61K 8/55; A61K 8/60; A61K 8/73; A61K 2800/48; A61K 2800/74; A61Q 11/00
See application file for complete search history.

(56) References Cited

U.S. PATENT DOCUMENTS

| | | |
|---|---|---|
| 6,350,436 B1 | 2/2002 | Glandorf et al. |
| 6,555,094 B1 | 4/2003 | Glandorf et al. |
| 6,685,920 B2 | 2/2004 | Baig |
| 6,696,045 B2 | 2/2004 | Yue |
| 6,714,309 B2 | 3/2004 | May |
| 7,387,774 B2 | 6/2008 | Faller |
| 8,795,637 B2 | 8/2014 | Deckner et al. |
| 8,906,347 B2 | 12/2014 | Strand |
| 9,155,769 B2 | 10/2015 | Hoke et al. |
| 9,687,427 B2 | 6/2017 | Li et al. |
| 10,172,770 B2 | 1/2019 | Rege |
| 10,213,368 B2 | 2/2019 | Li et al. |
| 10,214,368 B2 | 2/2019 | Demers |
| 10,258,549 B2 | 4/2019 | Baig |
| 10,258,550 B2 | 4/2019 | Baig |
| 10,357,438 B2 | 7/2019 | Jaracz |
| 10,369,090 B2 | 8/2019 | Baig |
| 10,376,451 B2 | 8/2019 | Baig |
| 10,470,985 B2 | 11/2019 | Baig |
| 10,548,827 B2 | 2/2020 | Hodgkinson |
| 10,596,086 B2 | 3/2020 | Ramji et al. |
| 10,646,417 B2 | 5/2020 | Mcgill |
| 2002/0106336 A1 | 8/2002 | Glandorf |
| 2008/0286214 A1 | 11/2008 | Brown |
| 2008/0311055 A1 | 12/2008 | Futterer |
| 2011/0020246 A1 | 1/2011 | Strand |
| 2011/0020247 A1 | 1/2011 | Strand |
| 2011/0020248 A1 | 1/2011 | Strand |
| 2012/0219606 A1* | 8/2012 | Deckner .................. A61K 8/25 424/53 |
| 2012/0276023 A1 | 11/2012 | Shimohirao |
| 2014/0037555 A1 | 2/2014 | Hoke, II |
| 2014/0127145 A1 | 5/2014 | Deckner |
| 2014/0227202 A1 | 8/2014 | Pilgaonkar |
| 2017/0105911 A1 | 4/2017 | Budde |
| 2017/0157171 A1 | 6/2017 | Gerard |
| 2017/0333310 A1 | 11/2017 | Subramanyam |
| 2017/0367939 A1 | 12/2017 | Thomson et al. |
| 2017/0367948 A1 | 12/2017 | Thomson et al. |
| 2018/0235853 A1 | 8/2018 | Brown et al. |
| 2019/0209448 A1 | 7/2019 | Dogu et al. |
| 2019/0298636 A1 | 10/2019 | Strand |
| 2020/0170902 A1 | 6/2020 | Ramji et al. |
| 2020/0188264 A1 | 6/2020 | Hodgkinson |
| 2020/0405593 A1 | 12/2020 | Baig et al. |
| 2020/0405594 A1 | 12/2020 | Baig et al. |
| 2020/0405595 A1 | 12/2020 | Gupta et al. |
| 2021/0346252 A1 | 11/2021 | Baig et al. |
| 2021/0346253 A1 | 11/2021 | Baig et al. |
| 2021/0346255 A1 | 11/2021 | Glandorf et al. |
| 2021/0346256 A1 | 11/2021 | Baig et al. |

FOREIGN PATENT DOCUMENTS

| | | |
|---|---|---|
| EP | 2281543 A1 | 2/2011 |
| WO | 2007076001 A2 | 7/2007 |
| WO | 2019183876 A1 | 10/2019 |

OTHER PUBLICATIONS

Notice of Allowance; Chinese Patent Application No. 202180033288.0 dated May 30, 2024; 3 pages.
Office Action; Chinese Patent Application No. 202180033288.0 dated Jan. 8, 2024; 12 pages.
PCT Search Report and Written Opinion for PCT/US2021/030754 dated Oct. 11, 2021, 12 pages.
All Office Actions; U.S. Appl. No. 17/308,081, filed May 5, 2021.
All Office Actions; U.S. Appl. No. 17/308,083, filed May 5, 2021.
All Office Actions; U.S. Appl. No. 17/308,085, filed May 5, 2021.
Deep Clean Fluoride Toothpaste, Mintel, Retrieved from Internet: http://www.gndp.com, Aug. 13, 2018, 4 pages.
Lolontika Hoque, "This is why you shouldn't swallow your toothpaste (besides it being totally disgusting), Spoon University, online retrieved from https://spoonuniversity.com/lifestyle/can-you-eat-toothpaste-this-is-why-you-shouldn-t", Jun. 26, 2017, 4 pages.
Sensitive Protect Smooth Mint Toothpaste, Mintel, Retrieved from Internet: http://www.gndp.com, Nov. 28, 2019, 4 pages.

* cited by examiner

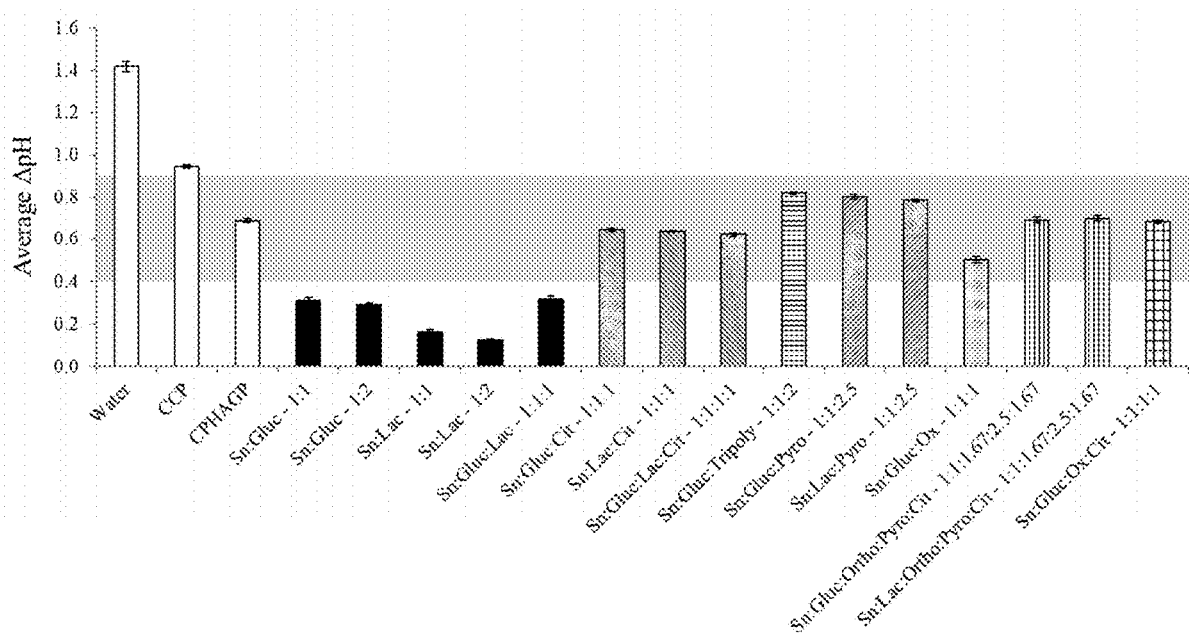

ORAL CARE COMPOSITIONS COMPRISING MONODENTATE AND POLYDENTATE LIGAND

FIELD OF THE INVENTION

The present invention relates to oral care compositions comprising tin, monodentate ligand, and polydentate ligand. The present invention also relates to improved ligand systems for stabilizing tin and increasing fluoride uptake and/or soluble tin.

BACKGROUND OF THE INVENTION

Oral care compositions have included antimicrobial agents, such as tin ions, to counter oral bacteria and to prevent and treat conditions caused by bacteria in the oral cavity, such as formation of dental plaque and calculus. The formation of dental plaque and calculus and failure to stop their proliferation are the primary cause of dental caries, gingivitis, periodontal disease, and tooth loss. Additionally, tin ions can deposit on surfaces in the oral cavity to provide protective functions, such as antierosion, antibacterial, and/or antisensitivity benefits.

However, tin can be challenging to properly formulate in oral care compositions due to reactivity between tin and other components of oral care compositions. Under-stabilizing or over-stabilizing tin can lead to lower availability of tin ions to provide the desired benefit. For example, if the tin is under-stabilized, the tin can react with other components of the oral care composition, such as silica, water, etc., which can lead to a lower amount of available tin ions. Additionally, the remaining under-stabilized tin, when delivered to the oral cavity, may be hyper-reactive with different oral surfaces, thus impeding the action of other ingredients or causing excess stain. In contrast, if the tin is over-stabilized or the chelant-tin interaction is too strong, tin ions will be tied up when delivered to the oral cavity, which can also lead to a lower amount of bioavailable tin ions to produce the desired oral care benefit.

Thus, the tin-chelant ratio and binding affinity must be carefully balanced to maximize the amount of available tin ions. As such, there is a need for oral care compositions comprising a high amount of available tin ions that are optimally bioavailable for the desired product benefit.

SUMMARY OF THE INVENTION

Disclosed herein is an oral care composition comprising (a) tin; (b) monodentate ligand; and (c) polydentate ligand, wherein the oral care composition has a tin to monodentate ligand to polydentate molar ratio of from about 1:0.5:0.5 to about 1:5:5.

Also disclosed herein is an oral care composition with an unexpectedly high fluoride uptake and/or unexpectedly high soluble tin amount.

Also disclosed herein is an oral care composition comprising (a) tin; (b) monodentate ligand, the monodentate ligand comprising carboxylic acid; and (c) polydentate ligand, the polydentate ligand comprising dicarboxylic acid, tricarboxylic acid, or combinations thereof, wherein the oral care composition has a tin to monodentate ligand to polydentate molar ratio of from about 1:0.5:0.5 to about 1:5:5.

Also disclosed herein is an oral care composition comprising (a) tin; (b) monodentate ligand, the monodentate ligand comprising carboxylic acid; and (c) polydentate ligand, the polydentate ligand comprising polyphosphate, wherein the oral care composition has a tin to monodentate ligand to polydentate molar ratio of from about 1:1:1 to about 1:5:5.

Also disclosed herein is an oral care composition comprising (a) stannous fluoride; (b) monodentate ligand; (c) polydentate ligand, wherein the oral care composition has a tin to monodentate ligand to polydentate molar ratio of from about 1:0.5:0.75 to about 1:5:5.

Also disclosed herein is an oral care composition comprising (a) tin; (b) monodentate ligand; and (c) polydentate ligand, wherein the oral care composition has a tin to monodentate ligand to polydentate molar ratio of from about 1:0.5:0.5 to about 1:5:5 and the composition is free of phytic acid.

Also disclosed herein is an oral care composition comprising (a) tin; (b) monodentate ligand; and (c) polydentate ligand, wherein the oral care composition has a tin to monodentate ligand to polydentate molar ratio of from about 1:0.5:0.5 to about 1:5:5 and the composition has a pH of greater than about 6.

Also disclosed herein is an oral care composition comprising (a) tin; (b) monodentate ligand; (c) polydentate ligand; and (d) thickening agent comprising xanthan gum, wherein the oral care composition has a tin to monodentate ligand to polydentate molar ratio of from about 1:0.5:0.5 to about 1:5:5.

BRIEF DESCRIPTION OF THE DRAWINGS

FIG. 1 displays the change in pH of an acid challenge after hydroxyapatite powder treated with a variety of oral care compositions was introduced to the acid challenge.

DETAILED DESCRIPTION OF THE INVENTION

The present invention is directed to oral care compositions with a tin-chelant and/or tin-ligand ratio that results in an optimally bioavailable and shelf-stable composition. Thus, the present invention provides efficacious oral hard tissue solubility reduction benefits and fluoride uptake benefits while simultaneously improving soluble tin throughout the shelf-life of the oral care composition. Such an achievement was realized with the discovery of optimum ratios of metal to monodentate ligand and metal to polydentate ligand that produces the desired stability and reactivity results.

The chelate effect postulates that complexes of polydentate ligands with a metal are more stable than the dentate-normalized equivalent of the monodentate-ligand-stabilized metal complex (e.g., 1 mole of a bidentate ligand in comparison to 2 moles of a similarly structured monodentate ligand) because of a reduction in molar entropy of the bidentate chelate with respect to the monodentate complex.

While not wishing to be bound by theory, in the cases of metals forming complexes in mixed polydentate/monodentate solutions, configurational restrictions in bonding geometries often result when using conventional stabilizers (e.g., citrate anion) that thusly favor the formation of metal-monodentate-polydentate complexes. Consider the case of stannous metal ion being chelated by citrate anion. $Sn^{2+}$ prefers a tetrahedral bonding geometry. The tridentate citrate anion can only occupy two of the four coordinating sites with stannous in this geometry because of steric restrictions. A monodentate ligand (e.g., gluconate) can thus participate in the complex at a third coordination site. The excess electron density (one electron from each of the three coordinating carboxylate anions minus the 2+ formal tin valency) is then distributed within the Sn bonding orbitals to the fourth coordination site that can acquire a hydrogen-bonded water or hydronium ion when in solution.

While not wishing to be bound by theory, if instead in the previous example, the molar ratio of citrate were increased from 1 to 2 and no monodentate ligand were present, the metal chelate would be over-stabilized resulting in a reduction of Sn bioavailability and a loss of oral care benefits. This is a direct result of the chelate effect. Additionally, the metal complex is under-stabilized if too little of the polydentate ligand is used in either the mixed- or polydentate-only cases also resulting in a loss of oral care benefits. Because of the unique properties of stannous ion in solution (tetrahedral bonding geometry with 2+ formal valence) and in the presence of mixed mono/polydentate ligands, $Sn^{2+}$ prefers mixed-dentate complexes. This is because, although two polydentate ligands can form a chelate complex, the resulting distribution of electron density is not favored thus providing an enthalpic penalty to formation of the complex.

Finally, in the case of monodentate-only stabilized metal complexes, there is no chelate effect and the stabilizing ligands can easily be replaced by chemical moieties with higher binding affinities. This results in under-stabilized stannous in the composition and loss to formula components (e.g., silica) over time. Thus, unexpectedly, an optimum mixture of mono- and polydentate coordinating ligands is needed to properly stabilize the metal ion without impeding its reactivity. As such, the present invention is directed to oral care compositions that provide an unexpectedly high soluble tin amount throughout the shelf life of the oral care composition while providing an optimally reactive stannous capable of providing tin-related oral care benefits without interfering with the activity of other reacting species.

In FIG. 1, we have illustrated the reduction in hydroxyapatite solubility reflected by the change in pH (ΔpH) after 5 minutes of a citric acid solution following the introduction of a slurry-supernatant-treated HAP powder. The different metal ligand ratios are indicated at the bottom. We have illustrated the region of optimum reactivity where the stabilizing Sn:monodentate:polydentate complex is neither too strong (thus preventing a solubility reduction benefit) nor too weak (thus inhibiting fluoride uptake). The optimum reactivity zone is indicated by the light gray band the cuts horizontally through the figure. The samples have been shaded according to: Experimental Controls (white bar); Monodentate Ligands Only (black bar); Citrate Polydentate (right diagonal hash); Tripolyphosphate Polydentate (horizontal hash); Pyrophosphate Polydentate (left diagonal hash); Oxalate Polydentate (dotted); Mixed Phosphate-Citrate Polydentate (vertical hash); Mixed Oxalate-Citrate Polydentate (cross hash). Abbreviations: CCP (Crest Cavity Protection, Procter & Gamble, Cincinnati, OH); CPHAGP (Crest ProHealth Advanced Gum Protection, Procter & Gamble, Cincinnati, OH); Sn (stannous); Gluc (gluconate); Lac (lactate); Ortho (orthophosphate); Ox (oxalate); Cit (citrate); Tripoly (tripolyphosphate); Pyro (pyrophosphate).

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied.

The term "oral care composition", as used herein, includes a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dentifrice composition", as used herein, includes tooth or subgingival-paste, gel, or liquid formulations unless otherwise specified. The dentifrice composition may be a single-phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

"Active and other ingredients" useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

The term "orally acceptable carrier" comprises one or more compatible solid or liquid excipients or diluents which are suitable for topical oral administration. By "compatible," as used herein, is meant that the components of the composition are capable of being commingled without interaction in a manner which would substantially reduce the composition's stability and/or efficacy. The carriers or excipients of the present invention can include the usual and conventional components of mouthwashes or mouth rinses, as more fully described hereinafter: Mouthwash or mouth rinse carrier materials typically include, but are not limited to one or more of water, alcohol, humectants, surfactants, and acceptance improving agents, such as flavoring, sweetening, coloring and/or cooling agents.

The term "substantially free" as used herein refers to the presence of no more than 0.05%, preferably no more than 0.01%, and more preferably no more than 0.001%, of an indicated material in a composition, by total weight of such composition.

The term "essentially free" as used herein means that the indicated material is not deliberately added to the composition, or preferably not present at analytically detectable levels. It is meant to include compositions whereby the indicated material is present only as an impurity of one of the other materials deliberately added.

The term "oral hygiene regimen' or "regimen" can be for the use of two or more separate and distinct treatment steps for oral health. e.g. toothpaste, mouth rinse, floss, toothpicks, spray, water irrigator, massager.

The term "total water content" as used herein means both free water and water that is bound by other ingredients in the oral care composition.

For the purpose of the present invention, the relevant molecular weight (MW) to be used is that of the material added when preparing the composition e.g., if the chelant is a citrate species, which can be supplied as citric acid, sodium citrate or indeed other salt forms, the MW used is that of the particular salt or acid added to the composition but ignoring any water of crystallization that may be present.

While compositions and methods are described herein in terms of "comprising" various components or steps, the compositions and methods can also "consist essentially of" or "consist of" the various components or steps, unless stated otherwise.

As used herein, the word "or" when used as a connector of two or more elements is meant to include the elements individually and in combination; for example, X or Y, means X or Y or both.

As used herein, the articles "a" and "an" are understood to mean one or more of the material that is claimed or described, for example, "an oral care composition" or "a bleaching agent."

All measurements referred to herein are made at about 23° C. (i.e. room temperature) unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, and so forth.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein.

The term "about" means that amounts, sizes, formulations, parameters, and other quantities and characteristics are not and need not be exact, but can be approximate and/or larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

The oral care composition can be in any suitable form, such as a solid, liquid, powder, paste, or combinations thereof. The oral care composition can be dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The components of the oral care composition can be incorporated into a film, a strip, a foam, or a fiber-based dentifrice composition.

The oral care compositions, as described herein, comprise tin, monodentate ligand, and polydentate ligand. Additionally, the oral care compositions can comprise other optional ingredients, as described below. The section headers below are provided for convenience only. In some cases, a compound can fall within one or more sections. For example, stannous fluoride can be a tin compound and/or a fluoride compound. Additionally, for example, oxalic acid, or salts thereof, can be a dicarboxylic acid, a polydentate ligand, and/or a whitening agent.

Tin

The oral care composition of the present invention comprise tin, which can be provided by a tin ion source. The tin ion source can be any suitable compound that can provide tin ions in an oral care composition and/or deliver tin ions to the oral cavity when the oral care composition is applied to the oral cavity. The tin ion source can comprise one or more tin containing compounds, such as stannous fluoride, stannous chloride, stannous bromide, stannous iodide, stannous oxide, stannous oxalate, stannous sulfate, stannous sulfide, stannic fluoride, stannic chloride, stannic bromide, stannic iodide, stannic sulfide, and/or mixtures thereof. The tin ion source can comprise stannous fluoride, stannous chloride, and/or mixture thereof. The tin ion source can also be a fluoride-free tin ion source, such as stannous chloride.

The oral care composition can comprise from about 0.0025% to about 5%, from about 0.01% to about 10%, from about 0.2% to about 1%, from about 0.4% to about 1%, or from about 0.3% to about 0.6%, by weight of the oral care composition, of tin and/or a tin ion source.

Monodentate Ligand

The oral care composition comprises a monodentate ligand having a molecular weight (MW) of less than 1000 g/mol. A monodentate ligand has a single functional group that can interact with the central atom, such as a tin ion. The monodentate ligand must be suitable for the use in oral care composition, which can be include being listed in Generally Regarded as Safe (GRAS) list with the United States Food and Drug Administration or other suitable list in a jurisdiction of interest.

The monodentate ligand, as described herein, can include a single functional group that can chelate to, associate with, and/or bond to tin. Suitable functional groups that can chelate to, associate with, and/or bond to tin include carbonyl, amine, among other functional groups known to a person of ordinary skill in the art. Suitable carbonyl functional groups can include carboxylic acid, ester, amide, or ketones.

The monodentate ligand can comprise a single carboxylic acid functional group. Suitable monodentate ligands comprising carboxylic acid can include compounds with the formula R—COOH, wherein R is any organic structure. Suitable monodentate ligands comprising carboxylic acid can also include aliphatic carboxylic acid, aromatic carboxylic acid, sugar acid, salts thereof, and/or combinations thereof.

The aliphatic carboxylic acid can comprise a carboxylic acid functional group attached to a linear hydrocarbon chain, a branched hydrocarbon chain, and/or cyclic hydrocarbon molecule. The aliphatic carboxylic acid can be fully saturated or unsaturated and have one or more alkene and/or alkyne functional groups. Other functional groups can be present and bonded to the hydrocarbon chain, including halogenated variants of the hydrocarbon chain. The aliphatic carboxylic acid can also include hydroxyl acids, which are organic compounds with an alcohol functional group in the alpha, beta, or gamma position relative to the carboxylic acid functional group. A suitable alpha hydroxy acid includes lactic acid and/or a salt thereof.

The aromatic carboxylic acid can comprise a carboxylic acid functional group attached to at least one aromatic functional group. Suitable aromatic carboxylic acid groups can include benzoic acid, salicylic acid, and/or combinations thereof.

The carboxylic acid can include formic acid, acetic acid, propionic acid, butyric acid, valeric acid, caproic acid, enanthic acid, caprylic acid, ascorbic acid, benzoic acid, caprylic acid, cholic acid, glycine, alanine, valine, isoleucine, leucine, phenylalanine, linoleic acid, niacin, oleic acid, propanoic acid, sorbic acid, stearic acid, gluconate, lactate, carbonate, chloroacetic acid, dichloroacetic acid, trichloroacetic acid, salts thereof, and/or combinations thereof.

The oral care composition can include from about 0.01% to about 10%, from about 0.1% to about 15%, from about 1% to about 5%, or from about 0.0001 to about 25%, by weight of the composition, of the monodentate ligand.

Polydentate Ligand

The oral care composition comprises polydentate ligand having a molecular weight (MW) of less than 1000 g/mol. A polydentate ligand has at least two functional groups that can interact with the central atom, such as a tin ion. Additionally, the polydentate ligand must be suitable for the use in oral care composition, which can be include being listed in Generally Regarded as Safe (GRAS) list with the United States Food and Drug Administration or another suitable list in a jurisdiction of interest.

The polydentate ligand, as described herein, can include at least two functional groups that can chelate to, associate with, and/or bond to tin. The polydentate ligand can comprise a bidentate ligand (i.e. with two functional groups), tridentate (i.e. with three functional groups), tetradentate (i.e. with four functional groups), etc.

Suitable functional groups that can chelate to, associate with, and/or bond to tin include carbonyl, phosphate, nitrate, amine, among other functional groups known to a person of ordinary skill in the art. Suitable carbonyl functional groups can include carboxylic acid, ester, amide, or ketones. Suitable compounds comprising phosphate include orthophosphate, phosphate, polyphosphate, salts thereof, and/or combinations thereof. Suitable phosphate compounds include phosphate salts, organophosphates, or combinations thereof. Suitable phosphate salts include salts of orthophosphate, hydrogen phosphate, dihydrogen phosphate, alkylated phosphates, polyphosphates, and/or combinations thereof.

The polydentate ligand can comprise two or more carboxylic acid functional groups. Suitable polydentate ligands comprising carboxylic acid can include compounds with the formula HOOC—R—COOH, wherein R is any organic structure. Suitable polydentate ligands comprising two or more carboxylic acid can also include dicarboxylic acid, tricarboxylic acid, tetracarboxylic acid, etc.

Other suitable polydentate ligands include compounds comprising at least two phosphate functional groups. Thus, the polydentate ligand can comprise polyphosphate, as described herein.

Other suitable polydentate ligands include hops beta acids, such as lupulone, colupulone, adlupulone, and/or combinations thereof. The hops beta acid can be synthetically derived and/or extracted from a natural source.

The polydentate ligand can comprise oxalic acid, oxalic acid, malonic acid, succinic acid, glutaric acid, adipic acid, pimelic acid, suberic acid, azerlaic acid, sebacic acid, undecanedioic acid, dodecanedioic acid, brassylic acid, thapsic acid, japanic acid, phellogenic acid, equisetolic acid, malic acid, tartaric acid, citric acid, phytic acid, pyrophosphate, tripolyphosphate, tetrapolyphosphate, hexametaphoshate, salts thereof, and/or combinations thereof.

The oral care composition can include from about 0.01% to about 10%, from about 0.1% to about 15%, from about 1% to about 5%, or from about 0.0001 to about 25%, by weight of the composition, of the polydentate ligand.

Ratio of Tin to Monodentate Ligand to Polydentate Ligand

The oral care composition, as described herein, comprises a ratio of tin to monodentate ligand to polydentate ligand that provides an unexpectedly high amount of soluble tin and/or a superior fluoride uptake. Suitable ratios of tin to monodentate ligand to polydentate ligand can be from about 1:0.5:0.5 to about 1:5:5, from about 1:0.5:0.75 to about 1:5:5, from about 1:1:1 to about 1:5:5, from about 1:1:0.5 to about 1:2.5:2.5, from about 1:1:1 to about 1:2:2, from about 1:0.5:0.5 to about 1:3:1, or from about 1:0.5:0.5 to about 1:1:3.

Desired herein are oral care compositions with a soluble Sn of at least about 1000 ppm, 2000 ppm, 4000 ppm, at least about 4500 ppm, at least about 5000 ppm, at least about 6000 ppm, and/or at least about 8000 ppm. Also desired herein are oral care compositions with a fluoride uptake of at least about 6.5 μg/cm², at least about 7.0 μg/cm², at least about 8.0 μg/cm², or at least about 9.0 μg/cm² after a time period of at least about 9 days, 30 days, 65 days, 75 days, 100 days, 200 days, 365 days and/or 400 days.

In total, while not wishing to be bound by theory it is believed that the soluble Sn amount is correlated to bioavailable Sn as it is freely available to provide an oral health benefit. Fully bound Sn (i.e. Sn that is overchelated) or precipitated Sn (i.e. insoluble tin salts, such as $Sn(OH)_2$ and/or Sn-based stains can form when Sn is underchelated) would not be included in the measurement for soluble Sn. Additionally, while not wishing to be bound by theory, it is believed that a carefully balanced ratio of Sn to monodentate and polydentate ligands can provide a high amount of bioavailable fluoride and Sn ions without some of the negatives to the use of cationic antimicrobial agents, such as surface staining. Thus, additional screening experiments were done to quantify and qualify the ranges and identities of monodentate and polydentate ligands.

Dicarboxylic Acid

The polydentate ligand can comprise dicarboxylic acid. The dicarboxylic acid comprises a compound with two carboxylic acid functional groups. The dicarboxylic acid can comprise a compound or salt thereof defined by Formula I.

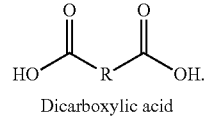

Formula I

Dicarboxylic acid

R can be null, alkyl, alkenyl, allyl, phenyl, benzyl, aliphatic, aromatic, polyethylene glycol, polymer, O, N, P, and/or combinations thereof.

The dicarboxylic acid can comprise oxalic acid, malonic acid, succinic acid, glutaric acid, adipic acid, pimelic acid, suberic acid, azerlaic acid, sebacic acid, undecanedioic acid, dodecanedioic acid, brassylic acid, thapsic acid, japanic acid, phellogenic acid, equisetolic acid, malic acid, tartaric acid, salts thereof, or combinations thereof. The dicarboxylic acid can comprise suitable salts of dicarboxylic acid, such as, for example, monoalkali metal oxalate, dialkali metal oxalate, monopotassium monohydrogen oxalate, dipotassium oxalate, monosodium monohydrogen oxalate, disodium oxalate, titanium oxalate, and/or other metal salts of oxalate. The dicarboxylic acid can also include hydrates of the dicarboxylic acid and/or a hydrate of a salt of the dicarboxylic acid.

The oral care composition can comprise from about 0.01% to about 10%, from about 0.1% to about 15%, from about 1% to about 5%, or from about 0.0001 to about 25%, by weight of the oral care composition, of dicarboxylic acid.

Tricarboxylic Acid

The polydentate ligand can comprise tricarboxylic acid. The tricarboxylic acid comprises a compound with three carboxylic acid functional groups. The tricarboxylic acid can comprise a compound or salt thereof defined by Formula II.

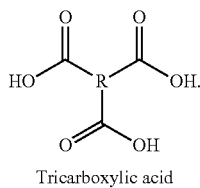

Formula II

Tricarboxylic acid

R can be alkyl, alkenyl, allyl, phenyl, benzyl, aliphatic, aromatic, polyethylene glycol, polymer, O, N, P, and/or combinations thereof.

The tricarboxylic acid can comprise citric acid, isocitric acid, aconitic acid, propane-1,2,3-tricarboxcylic acid, trimesic acid, any tricarboxylic acid in the citric acid cycle or Krebs Cycle, salts thereof, or combinations thereof. The tricarboxylic acid can comprise suitable salts of tricarboxylic acid, such as for example, sodium citrate.

The oral care composition can comprise from about 0.01% to about 10%, from about 0.1% to about 15%, from about 1% to about 5%, or from about 0.0001 to about 25%, by weight of the oral care composition, of tricarboxylic acid.

Polyphosphate

The polydentate ligand can comprise polyphosphate, which can be provided by a polyphosphate source. A polyphosphate source can comprise one or more polyphosphate molecules. Polyphosphates are a class of materials obtained by the dehydration and condensation of orthophosphate to yield linear and cyclic polyphosphates, such as phytic acid, of varying chain lengths. Thus, polyphosphate molecules are generally identified with an average number (n) of polyphosphate molecules, as described below. A polyphosphate is generally understood to consist of two or more phosphate molecules arranged primarily in a linear configuration, although some cyclic derivatives may be present.

Preferred polyphosphates are those having an average of two or more phosphate groups so that surface adsorption at effective concentrations produces sufficient non-bound phosphate functions, which enhance the anionic surface charge as well as hydrophilic character of the surfaces. Preferred in this invention are the linear polyphosphates having the formula: $XO(XPO_3)_nX$, wherein X is sodium, potassium, ammonium, or any other alkali metal cations and n averages from about 2 to about 21, from about 2 to about 14, or from about 2 to about 7. Alkali earth metal cations, such as calcium, are not preferred because they tend to form insoluble fluoride salts from aqueous solutions comprising a fluoride ions and alkali earth metal cations. Thus, the oral care compositions disclosed herein can be free of or substantially free of calcium pyrophosphate.

Some examples of suitable polyphosphate molecules include, for example, pyrophosphate (n=2), tripolyphosphate (n=3), tetrapolyphosphate (n=4), sodaphos polyphosphate (n=6), hexaphos polyphosphate (n=13), benephos polyphosphate (n=14), hexametaphosphate (n=21), which is also known as Glass H. Polyphosphates can include those polyphosphate compounds manufactured by FMC Corporation, ICL Performance Products, and/or Astaris.

The oral care composition can comprise from about 0.01% to about 15%, from about 0.1% to about 10%, from about 0.5% to about 5%, from about 1 to about 20%, or about 10% or less, by weight of the oral care composition, of the polyphosphate source. Alternatively, the oral care composition can be essentially free of, substantially free of, or free of polyphosphate. The oral care composition can be essentially free of, substantially free of, or free of cyclic polyphosphate. The oral care composition can be essentially free of, substantially free of, or free of phytic acid, which can lead to insoluble tin and/or zinc compounds.

Fluoride

The oral care composition can comprise fluoride, which can be provided by a fluoride ion source. The fluoride ion source can comprise one or more fluoride containing compounds, such as stannous fluoride, sodium fluoride, potassium fluoride, amine fluoride, sodium monofluorophosphate, zinc fluoride, and/or mixtures thereof.

The fluoride ion source and the tin ion source can be the same compound, such as for example, stannous fluoride, which can generate tin ions and fluoride ions. Additionally, the fluoride ion source and the tin ion source can be separate compounds, such as when the tin ion source is stannous chloride and the fluoride ion source is sodium monofluorophosphate or sodium fluoride.

The fluoride ion source and the zinc ion source can be the same compound, such as for example, zinc fluoride, which can generate zinc ions and fluoride ions. Additionally, the fluoride ion source and the zinc ion source can be separate compounds, such as when the zinc ion source is zinc phosphate and the fluoride ion source is stannous fluoride.

The fluoride ion source can be essentially free of or free of stannous fluoride. Thus, the oral care composition can comprise sodium fluoride, potassium fluoride, amine fluoride, sodium monofluorophosphate, zinc fluoride, and/or mixtures thereof.

The oral care composition can comprise a fluoride ion source capable of providing from about 50 ppm to about 5000 ppm, and preferably from about 500 ppm to about 3000 ppm of free fluoride ions. To deliver the desired amount of fluoride ions, the fluoride ion source may be present in the oral care composition at an amount of from about 0.0025% to about 5%, from about 0.01% to about 10%, from about 0.2% to about 1%, from about 0.5% to about 1.5%, or from about 0.3% to about 0.6%, by weight of the oral care composition. Alternatively, the oral care composition can comprise less than 0.1%, less than 0.01%, be essentially free of, be substantially free of, or free of a fluoride ion source.

Metal

The oral care composition, as described herein, can comprise metal, which can be provided by a metal ion source comprising one or more metal ions. The metal ion source can comprise or be in addition to the tin ion source and/or the zinc ion source, as described herein. Suitable metal ion sources include compounds with metal ions, such as, but not limited to Sn, Zn, Cu, Mn, Mg, Sr, Ti, Fe, Mo, B, Ba, Ce, Al, In and/or mixtures thereof. The metal ion source can be any compound with a suitable metal and any accompanying ligands and/or anions.

Suitable ligands and/or anions that can be paired with metal ion sources include, but are not limited to acetate, ammonium sulfate, benzoate, bromide, borate, carbonate, chloride, citrate, gluconate, glycerophosphate, hydroxide, iodide, oxalate, oxide, propionate, D-lactate, DL-lactate, orthophosphate, pyrophosphate, sulfate, nitrate, tartrate, and/or mixtures thereof.

The oral care composition can comprise from about 0.01% to about 10%, from about 1% to about 5%, or from about 0.5% to about 15% of metal and/or a metal ion source.

Zinc

The oral care composition can comprise zinc, which can be provided by a zinc ion source. The zinc ion source can comprise one or more zinc containing compounds, such as zinc fluoride, zinc lactate, zinc oxide, zinc phosphate, zinc chloride, zinc acetate, zinc hexafluorozirconate, zinc sulfate, zinc tartrate, zinc gluconate, zinc citrate, zinc malate, zinc glycinate, zinc pyrophosphate, zinc metaphosphate, zinc oxalate, and/or zinc carbonate. The zinc ion source can be a fluoride-free zinc ion source, such as zinc phosphate, zinc oxide, and/or zinc citrate.

The zinc and/or zinc ion source may be present in the total oral care composition at an amount of from about 0.01% to about 10%, from about 0.2% to about 1%, from about 0.5% to about 1.5%, or from about 0.3% to about 0.6%, by weight of the dentifrice composition. Alternatively, the oral care composition can be essentially free of, substantially free of, or free of zinc.

pH

The pH of the oral care compositions as described herein can be from about 4 to about 7, from about 4.5 to about 6.5, or from about 4.5 to about 5.5. The pH of the oral care compositions, as described herein, can also be at least about 6, at least about 6.5, or at least about 7. The pH of a mouthrinse solution can be determined as the pH of the neat solution. The pH of a dentifrice composition can be determined as a slurry pH, which is the pH of a mixture of the dentifrice composition and water, such as a 1:4, 1:3, or 1:2 mixture of the dentifrice composition and water. The pH of the oral care compositions as described herein have a preferred pH of from about 4 to about 10, from about 5 to about 9, from about 6 to 8, or about 7.

The oral care composition can comprise one or more buffering agents. Buffering agents, as used herein, refer to agents that can be used to adjust the slurry pH of the oral care compositions. The buffering agents include alkali metal hydroxides, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, citric acid, and sodium citrate. The oral care composition can comprise one or more buffering agents each at a level of from about 0.1% to about 30%, from about 1% to about 10%, or from about 1.5% to about 3%, by weight of the present composition.

Surfactants

The oral care composition can comprise one or more surfactants. The surfactants can be used to make the compositions more cosmetically acceptable. The surfactant is preferably a detersive material which imparts to the composition detersive and foaming properties. Suitable surfactants are safe and effective amounts of anionic, cationic, nonionic, zwitterionic, amphoteric and betaine surfactants, such as sodium lauryl sulfate, sodium lauryl isethionate, sodium lauroyl methyl isethionate, sodium cocoyl glutamate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine, sodium cocoyl glutamate, and the like. Sodium lauryl sulfate is a preferred surfactant. The oral care composition can comprise one or more surfactants each at a level from about 0.01% to about 15%, from about 0.3% to about 10%, or from about 0.3% to about 2.5%, by weight of the oral care composition.

Thickening Agent

The oral care composition can comprise one or more thickening agents. Thickening agents can be useful in the oral care compositions to provide a gelatinous structure that stabilizes the toothpaste against phase separation. Suitable thickening agents include polysaccharides, polymers, and/or silica thickeners. Some non-limiting examples of polysaccharides include starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; and mixtures thereof.

The thickening agent can comprise polysaccharides. Polysaccharides that are suitable for use herein include carageenans, gellan gum, locust bean gum, xanthan gum, carbomers, poloxamers, modified cellulose, and mixtures thereof. Carageenan is a polysaccharide derived from seaweed. There are several types of carageenan that may be distinguished by their seaweed source and/or by their degree of and position of sulfation. The thickening agent can comprise kappa carageenans, modified kappa carageenans, iota carageenans, modified iota carageenans, lambda carrageenan, and mixtures thereof. Carageenans suitable for use herein include those commercially available from the FMC Company under the series designation "Viscarin," including but not limited to Viscarin TP 329, Viscarin TP 388, and Viscarin TP 389.

The thickening agent can comprise one or more polymers. The polymer can be a polyethylene glycol (PEG), a polyvinylpyrrolidone (PVP), polyacrylic acid, a polymer derived from at least one acrylic acid monomer, a copolymer of maleic anhydride and methyl vinyl ether, a crosslinked polyacrylic acid polymer, of various weight percentages of the oral care composition as well as various ranges of average molecular ranges. The polymer can comprise polyacrylate crosspolymer, such as polyacrylate crosspolymer-6. Suitable sources of polyacrylate crosspolymer-6 can include Sepimax Zen™ commercially available from Seppic.

The thickening agent can comprise inorganic thickening agents. Some non-limiting examples of suitable inorganic thickening agents include colloidal magnesium aluminum silicate, silica thickeners. Useful silica thickeners include, for example, include, as a non-limiting example, an amorphous precipitated silica such as ZEODENT® 165 silica.

Other non-limiting silica thickeners include ZEODENT® 153, 163, and 167, and ZEOFREE® 177 and 265 silica products, all available from Evonik Corporation, and AEROSIL® fumed silicas.

The oral care composition can comprise from 0.01% to about 15%, from 0.1% to about 10%, from about 0.2% to about 5%, or from about 0.5% to about 2% of one or more thickening agents.

Abrasive

The oral care composition of the present invention can comprise an abrasive. Abrasives can be added to oral care formulations to help remove surface stains from teeth. Preferably, the abrasive is a calcium abrasive or a silica abrasive.

The calcium abrasive can be any suitable abrasive compound that can provide calcium ions in an oral care composition and/or deliver calcium ions to the oral cavity when the oral care composition is applied to the oral cavity. The oral care composition can comprise from about 5% to about 70%, from about 10% to about 60%, from about 20% to about 50%, from about 25% to about 40%, or from about 1% to about 50% of a calcium abrasive. The calcium abrasive can comprise one or more calcium abrasive compounds, such as calcium carbonate, precipitated calcium carbonate (PCC), ground calcium carbonate (GCC), chalk, dicalcium phosphate, calcium pyrophosphate, and/or mixtures thereof.

The oral care composition can also comprise a silica abrasive, such as silica gel (by itself, and of any structure), precipitated silica, amorphous precipitated silica (by itself, and of any structure as well), hydrated silica, and/or combinations thereof. The oral care composition can comprise from about 5% to about 70%, from about 10% to about 60%, from about 10% to about 50%, from about 20% to about 50%, from about 25% to about 40%, or from about 1% to about 50% of a silica abrasive.

The oral care composition can also comprise another abrasive, such as bentonite, perlite, titanium dioxide, alumina, hydrated alumina, calcined alumina, aluminum silicate, insoluble sodium metaphosphate, insoluble potassium metaphosphate, insoluble magnesium carbonate, zirconium silicate, particulate thermosetting resins and other suitable abrasive materials. The oral care composition can comprise from about 5% to about 70%, from about 10% to about 60%, from about 10% to about 50%, from about 20% to about 50%, from about 25% to about 40%, or from about 1% to about 50% of another abrasive.

Amino Acid

The oral care composition can comprise amino acid. The amino acid can comprise one or more amino acids, peptide, and/or polypeptide, as described herein.

Amino acids, as in Formula II, are organic compounds that contain an amine functional group, a carboxyl functional group, and a side chain (R in Formula III) specific to each amino acid. Suitable amino acids include, for example, amino acids with a positive or negative side chain, amino acids with an acidic or basic side chain, amino acids with polar uncharged side chains, amino acids with hydrophobic side chains, and/or combinations thereof. Suitable amino acids also include, for example, arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan, citrulline, ornithine, creatine, diaminobutanoic acid, diaminoproprionic acid, salts thereof, and/or combinations thereof.

Suitable amino acids include the compounds described by Formula III, either naturally occurring or synthetically derived. The amino acid can be zwitterionic, neutral, positively charged, or negatively charged based on the R group and the environment. The charge of the amino acid, and whether particular functional groups, can interact with tin at particular pH conditions, would be well known to one of ordinary skill in the art.

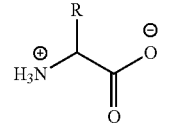

Formula III

Amino Acid.
R is any functional group

Suitable amino acids include one or more basic amino acids, one or more acidic amino acids, one or more neutral amino acids, or combinations thereof.

The oral care composition can comprise from about 0.01% to about 20%, from about 0.1% to about 10%, from about 0.5% to about 6%, or from about 1% to about 10% of amino acid, by weight of the oral care composition.

The term "neutral amino acids" as used herein include not only naturally occurring neutral amino acids, such as alanine, asparagine, cysteine, glutamine, glycine, isoleucine, leucine, methionine, phenylalanine, proline, serine, threonine, tryptophan, tyrosine, valine, but also biologically acceptable amino acid which has an isoelectric point in range of pH 5.0 to 7.0. The biologically preferred acceptable neutral amino acid has a single amino group and carboxyl group in the molecule or a functional derivative hereof, such as functional derivatives having an altered side chain albeit similar or substantially similar physio chemical properties. In a further embodiment the amino acid would be at minimum partially water soluble and provide a pH of less than 7 in an aqueous solution of 1 g/1000 ml at 25° C.

Accordingly, neutral amino acids suitable for use in the invention include, but are not limited to, alanine, aminobutyrate, asparagine, cysteine, cystine, glutamine, glycine, hydroxyproline, isoleucine, leucine, methionine, phenylalanine, proline, serine, taurine, threonine, tryptophan, tyrosine, valine, salts thereof, or mixtures thereof. Preferably, neutral amino acids used in the composition of the present invention may include asparagine, glutamine, glycine, salts thereof, or mixtures thereof. The neutral amino acids may have an isoelectric point of 5.0, or 5.1, or 5.2, or 5.3, or 5.4, or 5.5, or 5.6, or 5.7, or 5.8, or 5.9, or 6.0, or 6.1, or 6.2, or 6.3, or 6.4, or 6.5, or 6.6, or 6.7, or 6.8, or 6.9, or 7.0, in an aqueous solution at 25° C. Preferably, the neutral amino acid is selected from proline, glutamine, or glycine, more preferably in its free form (i.e. uncomplexed). If the neutral amino acid is in its salt form, suitable salts include salts known in the art to be pharmaceutically acceptable salts considered to be physiologically acceptable in the amounts and concentrations provided.

Whitening Agent

The oral care composition may comprise from about 0.1% to about 10%, from about 0.2% to about 5%, from about 1% to about 5%, or from about 1% to about 15%, by weight of the oral care composition, of a whitening agent. The whitening agent can be a compound suitable for whitening at least one tooth in the oral cavity. The whitening agent may include peroxides, metal chlorites, perborates, percarbonates, peroxyacids, persulfates, dicarboxylic acids, and combinations thereof. Suitable peroxides include solid peroxides, hydrogen peroxide, urea peroxide, calcium peroxide, benzoyl peroxide, sodium peroxide, barium peroxide, inorganic peroxides, hydroperoxides, organic peroxides, and mixtures thereof. Suitable metal chlorites include calcium chlorite, barium chlorite, magnesium chlorite, lithium chlorite, sodium chlorite, and potassium chlorite. Other suitable whitening agents include sodium persulfate, potassium persulfate, peroxydone, 6-phthalimido peroxy hexanoic acid, Pthalamidoperoxycaproic acid, or mixtures thereof.

Humectant

The oral care composition can comprise one or more humectants, have low levels of a humectant, or be free of a humectant. Humectants serve to add body or "mouth texture" to an oral care composition or dentifrice as well as preventing the dentifrice from drying out. Suitable humectants include polyethylene glycol (at a variety of different molecular weights), propylene glycol, glycerin (glycerol), erythritol, xylitol, sorbitol, mannitol, butylene glycol, lactitol, hydrogenated starch hydrolysates, and/or mixtures thereof. The oral care composition can comprise one or more humectants each at a level of from 0 to about 70%, from about 5% to about 50%, from about 10% to about 60%, or from about 20% to about 80%, by weight of the oral care composition.

Water

The oral care composition of the present invention can be a dentifrice composition that is anhydrous, a low water formulation, or a high water formulation. In total, the oral care composition can comprise from 0% to about 99%, about 20% or greater, about 30% or greater, about 50% or greater, up to about 45%, or up to about 75%, by weight of the composition, of water. Preferably, the water is USP water.

In a high water dentifrice formulation, the dentifrice composition comprises from about 45% to about 75%, by weight of the composition, of water. The high water dentifrice composition can comprise from about 45% to about 65%, from about 45% to about 55%, or from about 46% to about 54%, by weight of the composition, of water. The water may be added to the high water dentifrice formulation and/or may come into the composition from the inclusion of other ingredients.

In a low water dentifrice formulation, the dentifrice composition comprises from about 10% to about 45%, by weight of the composition, of water. The low water dentifrice composition can comprise from about 10% to about 35%, from about 15% to about 25%, or from about 20% to about 25%, by weight of the composition, of water. The water may be added to the low water dentifrice formulation and/or may come into the composition from the inclusion of other ingredients.

In an anhydrous dentifrice formulation, the dentifrice composition comprises less than about 10%, by weight of the composition, of water. The anhydrous dentifrice composition comprises less than about 5%, less than about 1%, or 0%, by weight of the composition, of water. The water may be added to the anhydrous formulation and/or may come into the dentifrice composition from the inclusion of other ingredients.

The dentifrice composition can also comprise other orally acceptable carrier materials, such as alcohol, humectants, polymers, surfactants, and acceptance improving agents, such as flavoring, sweetening, coloring and/or cooling agents.

The oral care composition can also be a mouth rinse formulation. A mouth rinse formulation can comprise from about 75% to about 99%, from about 75% to about 95%, or from about 80% to about 95% of water.

Other Ingredients

The oral care composition can comprise a variety of other ingredients, such as flavoring agents, sweeteners, colorants, preservatives, buffering agents, or other ingredients suitable for use in oral care compositions, as described below.

Flavoring agents also can be added to the oral care composition. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") or N-(Ethoxycarbonylmethyl)-3-p-menthanecarboxamide (known commercially as "WS-5"), and mixtures thereof. A flavor system is generally used in the compositions at levels of from about 0.001% to about 5%, by weight of the oral care composition. These flavoring agents generally comprise mixtures of aldehydes, ketones, esters, phenols, acids, and aliphatic, aromatic and other alcohols.

Sweeteners can be added to the oral care composition to impart a pleasing taste to the product. Suitable sweeteners include saccharin (as sodium, potassium or calcium saccharin), cyclamate (as a sodium, potassium or calcium salt), acesulfame-K, thaumatin, neohesperidin dihydrochalcone, ammoniated glycyrrhizin, dextrose, levulose, sucrose, mannose, sucralose, *stevia*, and glucose.

Colorants can be added to improve the aesthetic appearance of the product. Suitable colorants include without limitation those colorants approved by appropriate regulatory bodies such as the FDA and those listed in the European Food and Pharmaceutical Directives and include pigments, such as $TiO_2$, and colors such as FD&C and D&C dyes.

Preservatives also can be added to the oral care compositions to prevent bacterial growth. Suitable preservatives approved for use in oral compositions such as methylparaben, propylparaben, benzoic acid, and sodium benzoate can be added in safe and effective amounts.

Titanium dioxide may also be added to the present composition. Titanium dioxide is a white powder which adds opacity to the compositions. Titanium dioxide generally comprises from about 0.25% to about 5%, by weight of the oral care composition.

Other ingredients can be used in the oral care composition, such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, and the like.

Oral Care Composition Forms

Suitable compositions for the delivery of the tin, monodentate ligand, and/or polydentate ligand include emulsion compositions, such as the emulsions compositions of U.S. Patent Application Publication No. 2018/0133121, which is herein incorporated by reference in its entirety, unit-dose compositions, such as the unit-dose compositions of U.S. Patent Application Publication No. 2019/0343732, which is herein incorporated by reference in its entirety, leave-on oral care compositions, jammed emulsions, dentifrice compositions, mouth rinse compositions, mouthwash compositions, tooth gel, subgingival gel, mouth rinse, mousse, foam, mouth spray, lozenge, chewable tablet, chewing gum, tooth whitening strips, floss and floss coatings, breath freshening dissolvable strips, denture care products, denture adhesive products, or combinations thereof.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

Fluoride Uptake

The Enamel Fluoride Uptake by FDA Method 40 is a method used to determine the amount of fluoride delivered to demineralized enamel specimens from a single 30-minute treatment of 1:3 dentifrice slurry supernatant.

A core of sound human enamel with a diameter of 3-4 mm was extracted from whole human teeth. The cores were mounted on an acrylic rod and the surfaces were ground using 600 grit. The cores were then polished with $0.05\mu$ polish (Alumina Suspension Gamma B, MetLab Corp, catalog #M303-128). Specimens were stored in an airtight container above a small amount of deionized water (~1-5 mL) in a standard laboratory refrigerator (~2-4° C.).

Each enamel specimen was inspected and samples with large cracks or uneven calcification were discarded. Specimens were polished again for 10 minutes using 0.05p polish. Samples were sonicated with a sonicator in deionized water for 15-30 min. Enamel specimens were then rinsed with standard deionized water and wiped to remove any residual polish.

Enamel specimens were then demineralized. 25 mL of MHDP (N-2-hydroxyethyl, methane hydroxy diphosphonate) demineralization solution (0.025M lactic acid, $2 \times 10^4$M MHDP) was placed in a 30 mL plastic vial for each specimen. An enamel specimen was placed on the cap of each vial. Each cap was placed on the top of the vial to submerge the enamel specimen in the MHDP demineralization solution. The enamel specimen was not allowed to touch the bottom of the vial. Specimens were left in the demineralization solution for 48 hours at ambient conditions to form artificial caries lesions. The rods were tapped twice daily to remove any bubbles. After 48 hours, specimens were removed from the demineralization solution and rinsed thoroughly with deionized water.

If the sample was a paste dentifrice, 10 g of dentifrice was placed in a 50 mL tri-pour plastic beaker. 30 mL of deionized water was added to the beaker. An x-shaped stir bar was placed on top of the dentifrice in each beaker and the beaker was placed on a magnetic stir plate. The dentifrice was broken up with a wooden stick until the stir bar is capable of spinning freely at 300-400 rpm. The dentifrice slurry was stirred for 20 minutes. The slurry was transferred to a centrifuge tube and centrifuged for 30 minutes at 11,000 rpm.

Slurry supernatants were decanted into a 50 mL tri-pour plastic beaker. An x-shaped stir bar was placed in the beaker and the beaker was placed on a magnetic stir plate. The stir plate was turned to 300-400 rpm. Lesioned enamel specimens were suspended into each treatment. Each sample was treated for 30 minutes. After 30 minutes, each sample was rinsed with deionized water. Samples were stored in an airtight container above a small amount of deionized water (~1-5 mL) in a standard laboratory refrigerator (~2-4° C.).

The samples were analyzed for fluoride content analysis by collecting a portion of milled enamel powder following drilling to a depth of 50 micro-meters, dissolving that enamel in acid, then neutralizing and buffering it. Upon drilling a sample from the enamel specimen, the area of the enamel drilled was recorded.

Fluoride uptake was directly measured using a Fluoride Ion Specific Electrode (Thermo Scientific, Orion, 96-09-00, Waltham, MA). Each specimen sample was placed on the end of the electrode. A value of mV was recorded. This value was converted to ppm fluoride by using a standard curve of prepared fluoride standards. Fluoride uptake was calculated by dividing the mass of fluoride in μg by the total area sampled with the microdrill biopsy.

The Enamel Fluoride Uptake method is based upon FDA Test Method #40. The results for enamel fluoride uptake are provided herein.

Soluble Sn

This method is suitable for determination of soluble tin in oral care toothpaste or dentifrice compositions from about 5 to about 5,000 ppm Sn in the aqueous slurry supernatant. The slurry was prepared by mixing 1 part toothpaste with 3 parts water. An aliquot of slurry was acid digested, diluted, and analyzed by inductively coupled plasma optical emission spectrometry (ICP-OES) for each toothpaste measured. Results are reported here as ppm in the neat aqueous phase of the toothpaste and/or dentifrice.

Several standards and reagents were prepared prior to the beginning of the analysis. A 5% hydrochloric acid/5% Nitric acid rinse solution was prepared by transferring 100 mL each of concentrated HCl and concentrated $HNO_3$ using a graduated cylinder to a 2 L volumetric flask containing about 1 L of ultrapure, 18 MΩ (DI) water. The solution was swirled to mix and diluted to the mark of the graduated flask then mixed well by repeated flask inversion.

A 1000 mg/L tin and 1000 mg/L gallium standard solution were purchased (Sigma Aldrich, Merck KGaA, Darmstadt, Germany) for preparation of the standard solutions according to TABLE 1. A pipet was used to transfer accurate quantities of the standards to a 50 mL volumetric flask while a graduated cylinder was used for the concentrated acids. After transfer, the volumetric flask was filled to the line with DI water and mixed well.

TABLE 1

Soluble Sn Standard Solution Compositions

| Solution | Conc $HNO_3$ (mL) | Conc HCL (mL) | 1000 mg/L Sn Std (mL) | 1000 mg/L Ga Std (mL) |
|---|---|---|---|---|
| Cal Blank | 2.5 | 2.5 | 0 | 0.2 |
| Cal 10 mg/L Sn | 2.5 | 2.5 | 0.5 | 0.2 |
| LLOQ 0.5 mg/L Sn | 2.5 | 2.5 | 0.025 | 0.2 |
| QC 5 mg/L Sn | 2.5 | 2.5 | 0.25 | 0.2 |

Slurries were prepared by weighing 2.00 grams of sample into a tared round bottom 38 mL centrifuge tube containing 10 glass beads. The weight was recorded to a minimum of 0.001 g. Immediately before slurrying, 6.0 mL of DI water was transferred to the tubes. Tubes were capped and placed on a vortexer, mixing the samples for 60 minutes at 1200 rpm. The tubes were removed from the vortexer immediately following completion of the mixing cycle and placed in a centrifuge. They were centrifuged at 21,000 relative centrifugal force (RCF) for 10 minutes. Immediately following completion of centrifugation, the tubes were removed, and the supernatant was gently mixed by inverting slowly three times making sure the solid plug at the bottom of the centrifuge tube was not disturbed before the sample was decanted. The supernatant was then decanted into a15 mL screw cap sample tube, making sure most of the supernatant was transferred.

The supernatant samples were then digested by accurately weighing (to 0.001 g) a 0.5 mL aliquot of supernatant into a 50 mL Falcon tube. Then 2.5 mL of concentrated HCl and HNO$_3$ were added. The tubes were covered with a polypropylene watch glass and placed in a preheated block digester at 90° C. for 30 minutes. The samples were removed the from the heat, the watch class was rinsed three times with DI water (with about 1 mL each time), and that rinsate was added to the digested supernatant. The gallium standard (0.2 mL) was pipetted into the digested supernatant and then the supernatant samples were diluted to 50 mL with DI water. The tubes were capped and mixed. A digestion method blank was prepared in the same manner using 0.5 mL of DI water instead of supernatant. A method blank was prepared and analyzed for each set of hot block digestions if more samples were prepared than could fit into the hot block at once.

The ICP-OES (Perkin-Elmer 8300, Waltham, MA, USA) was operated by a trained and qualified operator with demonstrated capability of running the instrument and accurately determining the quantity of tin in oral care compositions. The ICP-OES operation parameters were selected based on the model and configuration according to the manufacturer's instructions. Samples were analyzed according to the following protocol:

1. The ICP-OES was preheated and optimized according to the manufacturer's guidelines. Recommended system checks were performed. The system was conditioned for 30 minutes prior to analysis by running the HCl/HNO$_3$ rinse solution through the sample introduction system.
2. The method for determining tin using a gallium internal standard at the manufacturer recommended wavelengths, integration times, and observation modes was loaded into the operating computer.
3. The 5% HCl/5% HNO$_3$ rinse solution was used to rinse the sample introduction system between the analysis of each blank, standard, or test solution.
4. Three to five readings were recorded for all solutions during analysis.
5. The calibration blank was analyzed.
6. The 10 ppm Sn standard was measured.
7. The 5 ppm Sn standard was measured.
8. The 0.5 ppm LLOQ tin standard was measured.
9. The method blank was measured.
10. The test solutions were measured.
11. The 5 ppm Sn standard was re-measured after every sixth test solution and after the last sample. Enough standard was made to complete the analysis.
12. The 0.5 ppm LLOQ tin standard was measured at the end of the sample analysis. The analysis was considered successful if the % relative standard deviation of the replicate readings for the 10 ppm and the 5 ppm tin standards was less than about 3%. The 5-ppm check standard was within 96-104% of its value. The LLOQ was within 75-125% of its value. The method blank showed less tin signal intensity than the LLOQ sample. The recovery of the internal standard in each analyzed solution was within 90-130% of its value.

The soluble tin was determined according to the following formula:

$$\text{Soluble Tin in Composition} = \frac{\text{Sn from } ICP\left(\frac{\mu g}{mL}\right) \times \text{Final volume of test solution (mL)}}{\text{Supernatant Weight (g)}} \times \frac{\text{Soluble Mass of Composition (g)} + \text{Slurry Water (g)}}{\text{Total Compoisition Mass (g)}}.$$

FORMULA IV

HAP Dissolution

The HAP dissolution method was designed to test the acid protection of a chosen test dentifrice. After treating hydroxyapatite powder (HAP) with test dentifrice slurries, the HAP was added to an acidic media and the change in pH was an indicator of the degree of surface adsorption and/or protection from acid.

Dentifrice slurries (1:3 paste:water) were prepared for all treatment compositions. Specifically, 10 g of dentifrice paste was combined with 30 g of deionized water in a 50 mL container with a stir bar. The dentifrice was broken up with a spatula until the stir bar moved freely at 300-400 rpm. The slurry was mixed on the stir plate for 10-20 minutes and/or until a uniform slurry was formed. The paste slurries were centrifuged at 15,000 rpm for 15 min to separate the solid components from the supernatant.

For each treatment, including for the water control, 0.300 g of hydroxyapatite powder (HAP) was placed into a 50 mL round bottom centrifuge tube with 4, 4 mm glass beads. For treatment with a dentifrice paste, 24 mL of the prepared dentifrice supernatant was added to the HAP. Each treated HAP sample was immediately vortex mixed at 2500 rpm for 2 minutes. All samples were then centrifuged at 15,000 rpm for 15 minutes. The liquid phase was decanted out of the centrifuge tube, which left a HAP pellet. The remaining HAP pellet was rinsed by adding deionized water, vortex mixing at 2500 rpm for 1 minute to completely disperse the pellet, centrifuging at 15,000 rpm for 15 minutes, and the liquid phase was decanted out of the centrifuge tube then discarded. This rinsing step was repeated two more times. The treated HAP pellet was dried in a 55° C. oven overnight.

Samples of HAP were analyzed for ΔpH. 25 mL of 10 mM citric acid (1.9212 g of citric acid in 1 L of deionized water) was added to a 50 mL beaker with a stir bar. The beaker was placed on a stir plate (Metrohm, Herisau, Switzerland, Model No. 728) and turned on. The Titrano pH electrode (Metrohm, Herisau, Switzerland, Model No. 719S) was placed in the stirring beaker with citric acid. After equilibration of the citric acid solution (until pH reads of 2.5±0.001 pH for 30 seconds), 50 mg of the dried HAP powder was added to the citric acid solution. The pH was recorded at 5 min. The ΔpH is determined by subtracting the pH reading at 5 minutes from the stable pH reading obtained immediately prior to adding the treated HAP powder.

TABLE 2

Compositions

| Component | Ex. 1 1:1:0.33 (wt %) | Ex. 2 1:1:0.67 (wt %) | Ex. 3 1:1:1 (wt %) | Ex. 4 1:2:1 (wt %) |
|---|---|---|---|---|
| Sorbitol | 48.0000 | 48.0000 | 48.0000 | 47.0000 |
| Treated Water | 21.1311 | 20.6161 | 20.0811 | 20.3791 |
| SnF$_2$ | 0.4540 | 0.4540 | 0.4540 | 0.4540 |
| SnCl$_2$ 10% silica blend | 0.5619 | 0.5619 | 0.5619 | 0.5619 |
| Sodium Gluconate | 1.3000 | 1.3000 | 1.3000 | 1.3000 |
| NaOH (50%) | 0.8700 | 0.8700 | 0.8700 | 0.8700 |
| Saccharin | 0.4000 | 0.4000 | 0.4000 | 0.4000 |
| Sucralose (25%) | 0.2000 | 0.2000 | 0.2000 | 0.2000 |
| Xanthan Gum | 0.8750 | 0.8750 | 0.8750 | 0.8750 |
| Carrageenan | 1.5000 | 1.5000 | 1.5000 | 1.5000 |
| Zinc Lactate | — | — | — | 0.735 |
| Zinc Citrate | 0.5330 | 0.5330 | 0.5330 | — |
| Na Citrate | — | 0.5150 | 1.0500 | 1.5500 |
| TiO$_2$ | 0.5000 | 0.5000 | 0.5000 | 0.5000 |
| Silica | 17.5000 | 17.5000 | 17.5000 | 17.5000 |
| SLSS (29%) | 5.0000 | 5.0000 | 5.0000 | 5.0000 |
| Flavor | 1.1750 | 1.1750 | 1.1750 | 1.1750 |

TABLE 2 describes the compositions tested for fluoride uptake and soluble Sn. Ex. 1 was a dentifrice composition with stannous fluoride and stannous chloride. Ex. 1 included at least two ligands for Sn: polydentate ligand (citrate) and monodentate ligand (gluconate). Citrate ions were provided by zinc citrate. Gluconate ions were provided by sodium gluconate. The molar ratio of Sn:mondentate:polydentate was 1 to 1 to 0.33 in Ex. 1.

Ex. 2 included monodentate ligand (gluconate) and polydentate ligand (citrate). Ex. 2 included additional amounts of polydentate ligand through the addition of sodium citrate. The molar ratio of Sn:monodentate:polydentate was 1 to 1 to 0.67. Ex. 3 included monodentate ligand (gluconate) and polydentate ligand (citrate). Ex. 3 included additional amounts of polydentate ligand through the addition of sodium citrate. The molar ratio of Sn:monodentate:polydentate was 1 to 1 to 1. Ex. 4 included monodentate ligand (gluconate and lactate) and polydentate ligand (citrate). The molar ratio of Sn:monodentate:polydentate was 1 to 2 to 1 with an additional amount of monodentate ligand. The additional monodentate ligand was provided by zinc lactate.

TABLE 3 showed the fluoride uptake of Ex. 1-4 under a variety of ligand ratios. The fluoride uptake increased with additional amounts of ligand. For example, as the Sn to monodentate to polydentate ligand ratio increased from 1 to 1 to 0.33 (Ex. 1) to 1 to 1 to 1 (Ex. 3), the fluoride uptake increased from 6.31 μg/cm$^2$ at 9 days to 7.61 μg/cm$^2$. This result was even more apparent at 230 days with a fluoride uptake of 5.86 μg/cm$^2$ for 1 to 1 to 0.33 (Ex. 1), but a fluoride uptake of 11.82 μg/cm$^2$ for 1 to 1 to 1 (Ex. 3). The fluoride uptake increased to 9.08 μg/cm$^2$ upon the addition of zinc lactate (Ex. 4). In total, the increased fluoride uptake trend is consistent for at least a year. These increases in fluoride uptake were unexpected because the amount of fluoride was held constant. Instead, the only formulation change was the balancing of ligands.

TABLE 3

| | | Fluoride Uptake (in μg/cm$^2$) | | | | | |
|---|---|---|---|---|---|---|---|
| Example | Sn:Mono:Poly[a] | ~9 d | ~30 d | ~65 d | ~85 d | ~230 d | ~400 d |
| 1 | 1:1:0.33 | 6.31 | 5.82 | 6.91 | 6.75 | 5.86 | 5.29 |
| 2 | 1:1:0.67 | 6.69 | 7.6 | 8.08 | 7.36 | 7.74 | 6.22 |
| 3 | 1:1:1 | 7.61 | 9.44 | 8.93 | 7.51 | 11.82 | 5.95 |
| 4 | 1:2:1 | 9.08 | 9.15 | 9.81 | 8.11 | 9.51 | 5.83 |

[a]Sn:Monodentate Ligand:Polydentate Ligand Molar Ratio

While not wishing to be bound by theory, we believe that the under-stabilized Sn in Ex. 1 results in Sn being hyper-reactive with the surface of enamel and depositing a layer on the surface that interferes with fluoride uptake. Sn is known to deposit onto the enamel surface as a means of providing resistance to plaque and dietary acids. Such a layer, if formed too thickly or too quickly, can interfere with the penetration of fluoride into caries lesions. It is believed that a carefully balanced ratio of Sn to monodentate and polydentate ligands can provide a high amount of bioavailable fluoride and Sn ions without some of the negatives to the use of cationic antimicrobial agents.

TABLE 4

| | | Soluble Sn (ppm) | | | | | |
|---|---|---|---|---|---|---|---|
| Example | Sn:Mono:Poly[a] | ~15 d | ~45 d | ~75 d | ~100 d | ~200 d | ~365 d |
| 1 | 1:1:0.33 | 3871 | 3314 | 2970 | 2863 | 2657 | 2653 |
| 2 | 1:1:0.67 | 4368 | 3894 | 3722 | 3203 | 3020 | 3268 |
| 3 | 1:1:1 | 4715 | 4276 | 4085 | 3856 | 3474 | 3299 |
| 4 | 1:2:1 | 5349 | 4200 | 4352 | 3856 | 3604 | 3429 |

[a]Sn:Monodentate Ligand:Polydentate Ligand Molar Ratio

TABLE 4 unexpectedly shows that providing additional amounts of polydentate ligand will lead to increased soluble Sn despite the amount of Sn being held constant. While not wishing to be bound by theory it is believed that the soluble Sn amount is correlated to bioavailable Sn as it is freely available to provide an oral health benefit. Fully bound Sn (i.e. Sn that is overchelated) or precipitated Sn (i.e. insoluble tin salts, such as Sn(OH)$_2$ and/or Sn-based stains can form when Sn is underchelated) would not be included in the measurement for soluble Sn. For example, as the Sn to monodentate to polydentate ligand ratio increased from 1 to 1 to 0.33 (Ex. 1) to 1 to 1 to 1 (Ex. 3), the soluble Sn amount increased from 3871 ppm to 4715 ppm at 15 days. This increase in soluble Sn was still apparent at 365 days with an increased soluble Sn amount from 2653 ppm (Ex. 1) to 3299 ppm (Ex. 4). There was also an increased amount of soluble Sn when an additional monodentate ligand was added to the 1 to 1 to 1 ratio (Ex. 4). The soluble Sn amount of Ex. 4 was at 5349 ppm at 15 days and 3429 ppm at 365 days.

While not wishing to be bound by theory, it is believed that a carefully balanced ratio of Sn to monodentate and polydentate ligands can provide a high amount of bioavailable fluoride and Sn ions without some of the negatives to the use of cationic antimicrobial agents, such as surface staining or interference with the uptake of fluoride. Thus, additional screening experiments were done to quantify and qualify the ranges and identities of monodentate and polydentate ligands.

The HAP dissolution method allows for the ability to screen far larger number of conditions in just a few days as opposed to fluoride uptake and/or soluble Sn measurements, which can take months. The HAP dissolution method measures the amount of material deposited on the surface of a hydroxyapatite (HAP) powder. The ΔpH is monitored as pre-treated hydroxyapatite powder is treated with an acid challenge. A lower ΔpH indicated more material deposited on the surface of the HAP powder particles because the acid was not able to dissolve the HAP coated with F and/or Sn. In contrast, a higher ΔpH is correlated with less material depositing on the surface of the HAP powder because the acid was able to dissolve the uncoated HAP.

A suitable composition should at least outperform (i.e. deposit more material) the positive control of Crest® Cavity Protection (1100 ppm NaF, no Sn ions) with a ΔpH less than about 0.9. Such performance would indicate that the Sn is not over-stabilized. However, an under-stabilized composition may be hyper reactive with the HAP powder resulting in thick, expansive, acid-resistant coatings on the HAP powder surface indicative of future interference with fluoride uptake into enamel. Consequently, the ΔpH should not be less than ca. 0.4. Such performance (i.e., ΔpH<ca. 0.4) would indicate that the Sn is under-stabilized. Thus, in total, the optimized, or Goldilocks range, for Sn stabilization is indicated by a ΔpH in HAP dissolution greater than about 0.4 but less than about 0.9 for a composition that has been formulated with approximately 1100 ppm fluoride. The range may shift depending on fluoride content; however, ΔpH of the Sn-containing composition should be less than its Sn placebo and more than about 0.4. The preferred zone relative to control formulas is illustrated in FIG. 1.

TABLE 5

Gluconate and Citrate Chelation

| Treatment | Sn:Mono:Poly | Average ΔpH | % RSD |
|---|---|---|---|
| Water | N/A | 1.42 | 1.69 |
| Crest ® Cavity Protection | N/A | 0.95 | 0.72 |
| Sn:Gluconate 1:1 | 1:1:0 | 0.31 | 4.95 |
| Sn Gluconate 1:2 | 1:2:0 | 0.29 | 3.00 |
| Sn:Gluconate:Citrate 1:1:1 | 1:1:1 | 0.64 | 1.32 |

TABLE 5 shows the HAP dissolution results for aqueous solutions comprising Sn and gluconate-citrate chelation system. Crest® Cavity Protection (CCP), the positive control, which included 1100 ppm of NaF without any chelation system, had a ΔpH of about 0.95. The other comparative compositions included $SnF_2$ and one or more ligands, such as monodentate and/or polydentate ligand. In the Sn:Gluconate 1:1 molar ratio, the ΔpH was determined to be about 0.29 while increasing the amount of the monodentate ligand to a 1:2 ratio resulted in a relatively unchanged ΔpH of about 0.31. As discussed herein, a very low ΔpH is indicative of under-stabilized Sn that is hyper reactive with the HAP surface and that will interfere with fluoride efficacy as observed by a reduced fluoride uptake. Unexpectedly, when a monodentate ligand was combined with a polydentate ligand, such as in the Sn:Gluconate:Citrate, the ΔpH was less than the ΔpH of Crest Cavity Protection indicating surface protection but not so low as the monodentate-only complex. This suggests that the Sn is properly stabilized to maintain high soluble Sn without being hyper reactive with the enamel surface. The Sn:Gluconate:Citrate molar ratio of 1:1:1 had a ΔpH of about 0.64. While not wishing to be bound by theory, it is believed that when the monodentate/polydentate ligand system is properly balanced with the amount of Sn, there is a maximum amount of bioavailable Sn without causing stain or interfering with fluoride uptake.

TABLE 6

Lactate Chelation System

| Treatment | Sn:Mono:Poly | Average ΔpH | % RSD |
|---|---|---|---|
| Water | N/A | 1.42 | 1.69 |
| Crest ® Cavity Protection | N/A | 0.95 | 0.72 |
| Sn:Gluconate 1:1 | 1:1:0 | 0.31 | 4.95 |
| Sn Gluconate 1:2 | 1:2:0 | 0.29 | 3.00 |
| Sn:Lactate 1:1 | 1:1:0 | 0.16 | 6.77 |
| Sn:Lactate 1:2 | 1:2:0 | 0.12 | 3.62 |
| Sn:Gluconate:Lactate 1:1:1 | 1:2:0 | 0.32 | 4.90 |
| Sn:Lactate:Citrate 1:1:1 | 1:1:1 | 0.64 | 0.72 |
| Sn:Gluc:Lactate:Citrate 1:1:1:1 | 1:2:1 | 0.62 | 1.46 |

TABLE 6 shows the impact of the addition of another monodentate ligand, lactate. As observed with gluconate, the use of a monodentate ligand, such as lactate in a Sn:monodentate molar ratio has an extremely low ΔpH, which likely indicated Sn-staining and/or a decrease in fluoride uptake. Importantly, adding more monodentate ligand, such as a Sn:monodentate molar ratio of 1:2 did not result in a ΔpH value within the necessary range. Additionally, having two different monodentate ligands did not result in a suitable value as Sn: Gluconate: Lactate at 1:1:1 resulted in a ΔpH of about 0.32. However, unexpectedly, the combination of a monodentate and polydentate ligand resulted in suitable ΔpH values. For example, Sn:Lactate:Citrate at 1:1:1 resulted in a ΔpH value of about 0.64 while a Sn:Gluconate:Lactate:Citrate at 1:1:1:1 (i.e. a Sn:monodentate:polydentate of 1:2:1) had a ΔpH value of about 0.62. Thus, both a monodentate and polydentate ligand are needed to carefully balance the amount of bioavailable Sn.

TABLE 7

Polyphosphates as Polydentate Ligands

| Treatment | Sn:Mono:Poly | Average ΔpH | % RSD |
|---|---|---|---|
| Water | N/A | 1.42 | 1.69 |
| Crest ® Cavity Protection | N/A | 0.95 | 0.72 |
| Sn:Gluc:Tripoly 1:2:1 | 1:2:1 | 0.82 | 0.81 |
| Sn:Gluc:Ortho:Pyro:Cit 1:1:1.67:2.5:1.67 | 1:1:5.84 | 0.69 | 1.72 |
| Sn:Lac:Ortho:Pyro:Cit 1:1:1.67:2.5:1.67 | 1:1:5.84 | 0.70 | 1.84 |
| Sn:Gluc:Pyro 1:1:2.5 | 1:1:2.5 | 0.80 | 1.58 |
| Sn:Lac:Pyro 1:1:2.5 | 1:1:2.5 | 0.79 | 0.83 |

TABLE 7 shows that other suitable monodentate ligands include phosphate-based compounds and that other suitable polydentate ligands include polyphosphates. As observed with citrate, the use of a polydentate ligand, such as phosphate polydentate ligands (Ortho, Pyro, Tripoly) in a Sn:monodentate:polydentate molar ratio has, unexpectedly, resulted in suitable ΔpH values. For example, Sn:Gluc:Tripoly 1:2:1 had a ΔpH of about 0.82, which was within the desired range. More complicated systems of multiple monodentate ligands and multiple polydentate ligands were also beneficial if properly balanced.

TABLE 8

| Oxalate Chelation System | | | |
|---|---|---|---|
| Treatment | Sn:Mono:Poly | Average ΔpH | % RSD |
| Water | N/A | 1.42 | 1.69 |
| Crest ® Cavity Protection | N/A | 0.95 | 0.72 |
| Sn:Gluc:Oxalate 1:1:1 | 1:1:1 | 0.50 | 3.24 |
| Sn:Gluc:Oxalate:Cit 1:1:2 | 1:1:2 | 0.68 | 1.05 |

TABLE 8 shows that oxalate and other dicarboxylic acids can also act as suitable polydentate ligands. For example, Sn:Gluc:Oxalate 1:1:1 had a ΔpH of about 0.50, which was within the preferred range.

TABLE 9 shows additional solution compositions with a variety of Sn:Mono:Poly ratios. Ex. A is a $SnF_2/SnCl_2$ dentifrice with gluconate and citrate at a Sn:Mono:Poly ratio of 1:1:0.33. Ex. B adds additional citrate ions (polydentate ligand) compared with Ex. A and has a Sn:Mono:Poly ratio of 1:1:0.67. Ex. C adds even more citrate ions (polydentate ligand) and has a Sn:Mono:Poly ratio of 1:1:1. Ex. D differs from Ex. A by adding phosphate ions (polydentate ligand) and has a Sn:Mono:Poly ratio of 1:1.5:0.73. Ex. E differs from Ex. D by adding even more phosphate ions (polydentate ligand) and has a Sn:Mono:Poly ratio of 1:1:1.63.

TABLE 10 shows the impact of the Sn:Mono:Poly ratios on the amount of soluble Sn and fluoride uptake. Unexpectedly, the fluoride uptake increases upon the addition of polydentate ligand, but not increasing amount of monodentate ligands. For example, when the Sn:Mono:Poly ratio increases from 1:1:0.33 to 1:1:0.67 to 1:1:1, the fluoride uptake increases from 6.72 µg/cm² to 7.18 µg/cm² to 8.00 µg/cm². At the same time, the amount of soluble Sn remains high (at least about 8000 ppm Sn). In contrast, when the Sn:Mono:poly ratio increases from 1:1:0.33 to 1:1:0.73 to 1:1:1.63, the fluoride uptake still increases from 6.72 µg/cm² to 6.99 µg/cm² to 10.83 µg/cm², but the soluble Sn drops dramatically from at least about 8000 ppm to 3700 ppm at 1:1:0.73 to 1600 ppm at 1:2:0.33. This indicated that while fluoride remained bioavailable, Sn ions were overchelated with too much phosphate polydentate present.

TABLE 9

| | Solution Compositions | | | | |
|---|---|---|---|---|---|
| | Ex. A | Ex. B | Ex. C | Ex. D | Ex. E |
| Sorbitol | 66.0179 | 65.6252 | 65.2694 | 65.7145 | 65.8512 |
| Water | 29.0759 | 28.8945 | 28.7450 | 28.9588 | 29.0093 |
| $SnF_2$ | 0.6240 | 0.6200 | 0.6169 | 0.6213 | 0.6225 |
| $SnCl_2$[a] | 0.7725 | 0.7675 | 0.7633 | 0.7691 | 0.7705 |
| Sodium Gluconate | 1.7857 | 1.7759 | 1.7653 | 1.7795 | 1.7819 |
| NaOH[b] | 0.9914 | 0.8918 | 0.7574 | 1.0165 | — |
| Zinc Citrate | 0.7326 | 0.7287 | 0.7240 | 0.7294 | 0.7307 |
| $SnCl_2$[c] | — | — | — | — | — |
| NaF | — | — | — | — | — |
| Sodium Citrate | — | 0.6963 | 1.3587 | — | — |
| $NaH_2PO_4$ | — | — | — | 0.4109 | 1.2339 |
| Sn:Mono:Poly | 1:1:0.33 | 1:1:0.67 | 1:1:1 | 1:1:0.73 | 1:1.163 |

[a]10% Silica Blend

[b]50 % solution in water

[c]Pure Solid

TABLE 10

Fluoride Uptake and Soluble Sn

| Example | Sn:Mono:Poly[a] | Fluoride Uptake (μg F/cm$^2$) | Soluble Sn (ppm) | Sn Added (ppm) |
|---|---|---|---|---|
| Ex. A | 1:1:0.33 | 6.72 | 8078 | 8384 |
| Ex. B | 1:1:0.67 | 7.18 | 8158 | 8330 |
| Ex. C | 1:1:1 | 8 | 8278 | 8288 |
| Ex. D | 1:1:073 | 6.99 | 3715 | 8348 |
| Ex. E | 1:1:1.63 | 10.83 | 1640 | 8364 |

[a]Sn:Monodentate Ligand:Polydentate Ligand Molar Ratio

In total, as described herein, stannous fluoride-based compositions can be extremely complex to formulate. At a neutral pH, a chelant system comprising monodentate and polydentate ligands can carefully balance the chelation of SnF$_2$ without causing Sn surface staining or sacrificing fluoride uptake values.

As shown in TABLEs 2-10, compositions desired herein include compositions comprising tin, monodentate ligand, and polydentate ligand, wherein the ratio of tin to monodentate ligand to polydentate ligand (tin:monodentate:polydentate) is from about 1:0.5:0.5 to about 1:5:5, from about 1:1:0.5: about 1:2.5:2.5, from about 1:1:1 to about 1:2:2, from about 1:0.5:0.5 to about 1:3:1, or from about 1:0.5:0.5 to about 1:1:3.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
   (a) tin, wherein the tin comprises stannous fluoride, stannous chloride, or combinations thereof;
   (b) monodentate ligand, wherein the monodentate ligand comprises a compound comprising a single functional group capable of chelating tin, and wherein the monodentate ligand comprises carboxylic acid or a salt thereof, wherein the carboxylic acid comprises aliphatic carboxylic acid, sugar acid, salts thereof, or combinations thereof;
   (c) polydentate ligand, wherein the polydentate ligand comprises a compound comprising at least two functional groups capable of chelating tin, wherein the polydentate ligand comprises a bidentate ligand and/or a tridentate ligand, and wherein the polydentate ligand comprises carboxylic acid, phosphate, polyphosphate, or combinations thereof, wherein the carboxylic acid comprises dicarboxylic acid, tricarboxylic acid, salts thereof, or combinations thereof; and
   (d) a fluoride source,
   wherein the oral care composition has a tin to monodentate ligand to polydentate ligand molar ratio of 1:1:1 to 1:2.5:2.5.

2. The oral care composition of claim 1, wherein the sugar acid comprises aldonic acid, ulsonic acid, uronic acid, aldaric acid, salts thereof, or combinations thereof.

3. The oral care composition of claim 2, wherein the sugar acid comprises gluconate.

4. The oral care composition of claim 1, wherein the aliphatic carboxylic acid comprises linear saturated carboxylic acid, linear unsaturated carboxylic acid, alpha hydroxy acid, beta hydroxy acid, gamma hydroxy acid, amino acid, salts thereof, or combinations thereof.

5. The oral care composition of claim 4, wherein the amino acid comprises glycine, alanine, valine, isoleucine, tryptophan, phenylalanine, proline, methionine, leucine, serine, threonine, tyrosine, asparagine, glutamine, cysteine, citrulline, aspartic acid, glutamic acid, lysine, arginine, histidine, or combinations thereof.

6. The oral care composition of claim 4, wherein the alpha hydroxy acid comprises lactate.

7. The oral care composition of claim 1, wherein the phosphate comprises inorganic phosphate salt, organophosphate, or combinations thereof.

8. The oral care composition of claim 7, wherein the phosphate salt comprises orthophosphate, hydrogen phosphate, dihydrogen phosphate, or combinations thereof.

9. The oral care composition of claim 1, wherein the dicarboxylic acid comprises a compound with the formula HO2C-R-CO2H, wherein R is aliphatic, aromatic, or combinations thereof.

10. The oral care composition of claim 1, wherein the dicarboxylic acid comprises oxalic acid, malonic acid, succinic acid, glutaric acid, adipic acid, pimelic acid, suberic acid, azerlaic acid, sebacic acid, undecanedioic acid, dodecanedioic acid, brassylic acid, thapsic acid, japanic acid, phellogenic acid, equisetolic acid, salts thereof, or combinations thereof.

11. The oral care composition of claim 1, wherein the tricarboxylic acid comprises citric acid, isocictric acid, aconitic acid, propane-1,2,3-tricarboxylic acid, trimesic acid, salts thereof, or combinations thereof.

12. The oral care composition of claim 1, wherein the polyphosphate comprises pyrophosphate, tripolyphosphate, tetrapolyphosphate, hexametaphosphate, or combinations thereof.

13. The oral care composition of claim 1, wherein the composition comprises zinc.

14. The oral care composition of claim 13, wherein the zinc comprises zinc citrate, zinc lactate, zinc oxide, zinc phosphate, or combinations thereof.

15. The oral care composition of claim 1, wherein the oral care composition comprises no added water, or comprises water.

16. The oral care composition of claim 15, wherein the oral care composition comprises up to 45%, by weight of the composition, of water.

17. The oral care composition of claim 1, wherein the oral care composition comprises a dentifrice composition, a unit-dose oral care composition, an emulsion composition, or a leave-on oral care composition.

\* \* \* \* \*